United States Patent [19]

Koehler et al.

[11] 4,289,589

[45] Sep. 15, 1981

[54] SEPARATING TOLUENE DIISOCYANATE AND/OR HIGHER BOILING SOLVENTS FROM DISTILLATION RESIDUES OF THE TOLUENE DIISOCYANATE MANUFACTURE USING A FLUIDIZED BED

[75] Inventors: Waldemar Koehler, Frankenthal, Fed. Rep. of Germany; Bernd Blumenberg, East Baton Rouge, La.; Ludwig Vogel, Frankenthal; Eckhard Hetzel, Bobenheim-Roxheim, both of Fed. Rep. of Germany

[73] Assignee: BASF Aktiengesellschaft, Ludwigshafen, Fed. Rep. of Germany

[21] Appl. No.: 135,303

[22] Filed: Mar. 31, 1980

[30] Foreign Application Priority Data

Apr. 19, 1979 [DE] Fed. Rep. of Germany ....... 2915830

[51] Int. Cl.³ ................... B01D 3/10; C07C 119/04
[52] U.S. Cl. ........................................ 203/49; 203/88; 203/89; 203/90
[58] Field of Search ............... 203/39, 49, 89, 90, 203/99, 100, DIG. 11, DIG. 14, DIG. 16, DIG. 25, 88; 23/294 R, 313 FB; 260/453 SP; 159/4 R, 4 E, 4 GC, 16 R, DIG. 3; 432/15; 110/245

[56] References Cited

U.S. PATENT DOCUMENTS 3,457,291  7/1969  Baylor ........................ 260/453 SP
3,897,314  7/1975  Liebsch et al. ............... 260/453 SP

OTHER PUBLICATIONS

"Chemical Engineer's Handbook", Perry, 4th Ed., 1966, pp. 17-23 to 17-26, 20-50 to 20-54.

*Primary Examiner*—Frank Sever
*Attorney, Agent, or Firm*—H. Lawrence Jones

[57] ABSTRACT

A process for separating toluene diisocyanate and/or higher boiling solvents from distillation residues obtained from the phosgenation of toluene diamine in the presence of solvents wherein the separation takes place in a fluidized bed at temperatures of 140° C. to 280° C.

9 Claims, 1 Drawing Figure

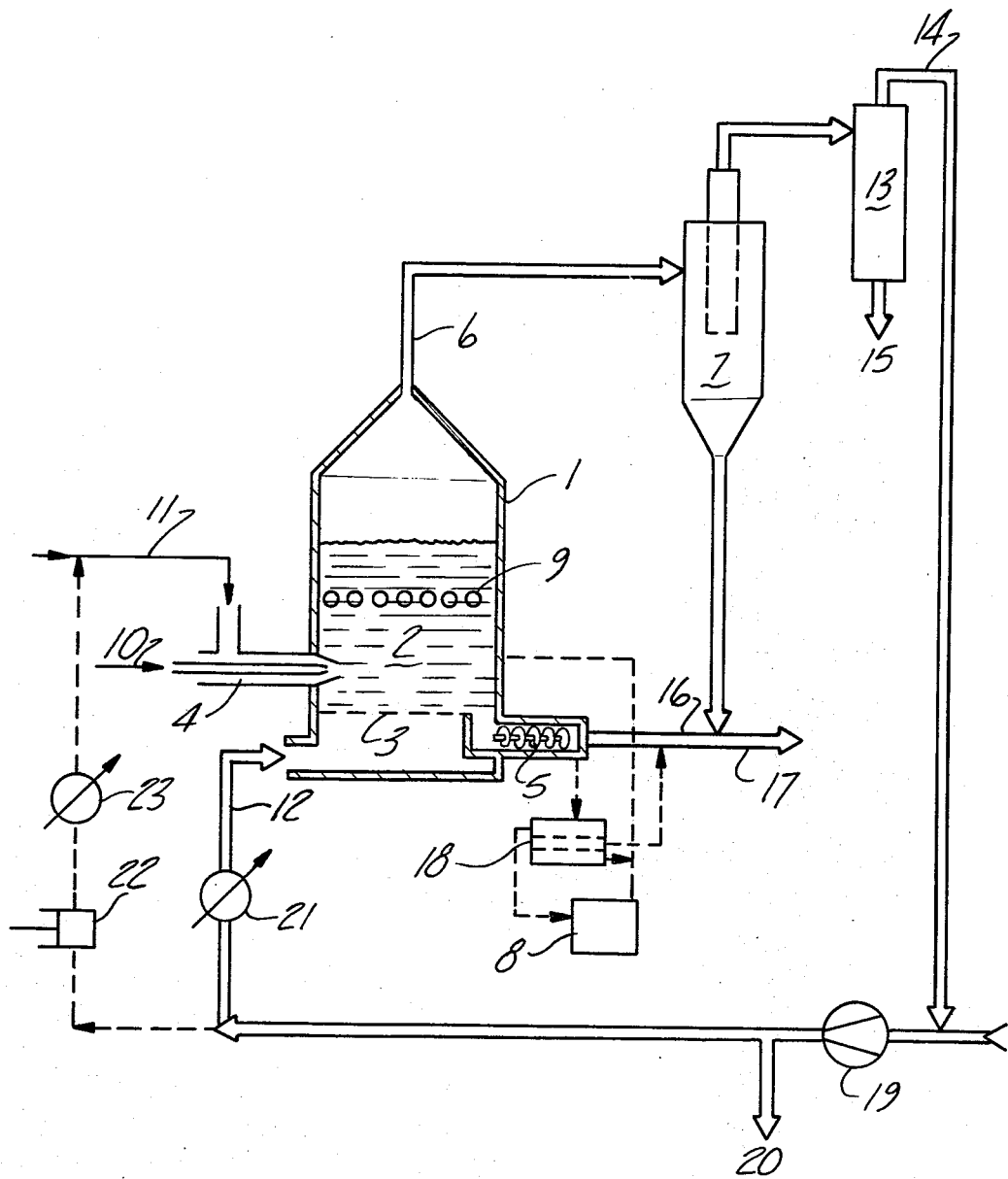

SEPARATING TOLUENE DIISOCYANATE AND/OR HIGHER BOILING SOLVENTS FROM DISTILLATION RESIDUES OF THE TOLUENE DIISOCYANATE MANUFACTURE USING A FLUIDIZED BED

BACKGROUND OF THE INVENTION

1. Field of the Invention

The invention relates to the separation of toluene diisocyanate and/or higher boiling solvents from distillation residues by evaporating the residue in a fluidized bed at temperatures of 140° C. to 280° C. The distillation residues are produced during the preparation of toluene diisocyanate by the phosgenation of toluene diamine.

2. Description of the Prior Art

Ullmann's *Encyclopedia of Technical Chemistry*, 4th Edition (1977), Vol. 13, p. 351, discloses the reaction of toluene diamine with phosgene to produce toluene diisocyanate in the presence of an organic solvent, such as monochlorobenzene or o-dichlorobenzene which boils at a lower temperature than toluene diisocyanate. The use of solvents boiling at higher temperatures then toluene diisocyanate has also been disclosed. These solvents include methyldiphenylmethane, tetrahydronaphthylene, or alkylisophthalate (the latter in French Pat. No. 1 476 755). The phosgenation is generally carried out in two stages, initially at temperatures of 0° C. to 100° C. and subsequently at temperatures from 150° C. to 180° C. The residual phosgene is then removed from the reaction solution by distillation or by passing nitrogen through the solution. The reaction solution is then distilled into toluene diisocyanate, the solvent, and phosgenation by-products, which are primarily non-volatile residues.

If a solvent is used for the phosgenation, boiling lower than toluene diisocyanate, it is distilled off first during further processing. This leaves a crude toluene diisocyanate mixture which consists of 65 weight percent to 98 weight percent of toluene diisocyanate, 0 weight percent to 10 weight percent of lower-boiling solvent, and 2 weight percent to 25 weight percent of non-volatile residues. If a solvent is used boiling higher than toluene diisocyanate, the toluene diisocyanate alone or a mixture of toluene diisocyanate and part of the higher-boiling solvent is initially distilled off. This leaves a residue mixture 65 weight percent to 89 weight percent of higher-boiling solvents, 0 weight percent to 10 weight percent of residual toluene diisocyanate, and 2 weight percent to 25 weight percent of nonvolatile residues. The residues may be totally or partially dissolved or partially suspended.

The above-mentioned mixtures are now further concentrated by means of distillation in the first case to obtain the toluene diisocyanate and in the latter case, to reclaim the higher-boiling solvents. A distillation residue is obtained which still contains considerable quantities of toluene diisocyanate and/or higher-boiling solvents normally between 20 weight percent and 80 weight percent hereinafter sometimes referred to as desired product. Depending upon the manufacturing conditions, the residual components of the distillation residue primarily consist of 1 weight percent to 80 weight percent of urea compounds, 0 weight percent to 40 weight percent of uretdione, 0 weight percent to 60 weight percent of isocyanuric esters, 0.5 weight percent to 20 weight percent of carbodiimides, and 5 weight percent to 95 weight percent of higher-condensing or polymeric materials.

The reclaiming of toluene diisocyanate and/or the higher-boiling solvents is of primary importance for the profitability of the manufacturing process. Various processes were developed for reclaiming isocyanate from residue mixtures. German Patent Application No. 12 43 178, for instance, describes an extraction process. British Pat. No. 1 117 066 and German Patent Application No. 12 31 689 describe distillation processes. German Application No. 19 62 598 relates to a hydrolysis process with subsequent phosgenation of the hydrolysis products. A drawback of the above-mentioned processes is that large quantities of solvents are required for isolating the isocyanate. These solvents have to be purified in separate expensive process stages.

In order to avoid these drawbacks, the distillation residue may be removed by screw conveyors. The residue may be fed into a heated packed bed equipped with a screw agitator so that it descends when agitated together with the solids material in the vertical center section, loses the volatile components at the bottom, and moves upwards along the peripheral zones to form a dry solid residue (German Published Application No. 24 52 805). The latter process is for the separation of toluene diisocyanate as well as for higher-boiling solvents. Although these processes show rather favorable results, they also have certain drawbacks. One drawback, for instance, is that the equipment has moveable parts upon which the chlorine and chloride-containing distillation residues have a strongly corrosive effect.

It was known that packed materials can be dried and cooled with the aid of fluidized beds [Machinenmarkt, Wuerzburg, 18 (1975) 79, pages 1480 to 1973].

SUMMARY OF THE INVENTION

The purpose of this invention was to develop a process for separating toluene diisocyanate and/or higher-boiling solvents from distillation residues that formed during the manufacture of toluene diisocyanate without additional extraction, distillation, or the use of solvents.

DESCRIPTION OF THE PREFERRED EMBODIMENTS

The invention relates to a process for the separation of toluene diisocyanate and/or higher boiling solvents from distillation residues obtained during the reaction of toluene diamine with phosgene in the presence of solvents and subsequent distillation of the reaction solution, comprising treating the distillation residues in a fluidized bed at temperatures of 140° C. to 280° C.

It is particularly surprising that the highly viscous to solid distillation residues, injected into the fluidized bed either in a totally or partially molten state, do not plug the openings in the gas ports of the fluidized bed reactor or cake together to form large agglomerates which can no longer be fluidized under economic conditions, but form a fluidizable material which can be discharged from the fluidized bed in a continuous manner. In spite of the wide distribution of residence times in the fluidized bed, the desired product to be separated—in the case of toluene diisocyanate these are common isomer mixtures of 2,4- and 2,6-toluene diisocyanate—is not heat damaged and correspondingly, an additional residue formation is not noticed. The desired product of the distillation residues is reclaimed at a high yield rate.

Another advantage is that the device may not have any mechanically moving or moveable parts as are encountered in screw conveyors or in agitated mixed beds. This results in low breakdown susceptibility, low maintenance and investment cost, and high yields. The separation of the desired product takes place under normal pressure, eliminating sealing problems; the required heat can be easily introduced by means of the fluidizing gas and can be transferred to the fluidized bed, and auxiliary solvents are not required.

Finally, another advantage of the process of this invention is that the dry residue, which is free of desired product, is obtained in a form which can be easily handled, pours easily, and is low in dust.

Normal fluidized bed units are well suited for implementing the process of this invention. Referring now more particularly to the drawing, there is shown a preferably used fluidized bed unit which primarily consist of a cylindrical fluidized bed reactor (1), the ratio of whose internal diameter to its length is generally 1:0.5 to 1:7, preferably 1:1 to 1:3; the fluidized bed (2); a fluidizing gas entry tray (3) which may consist of a sinter tray with a round-holed or bell-shaped plate or a conical finely-perforated thin-gauge plate; a product input jet (4); a discharge (5) which may contain a screw conveyor; an offgas exhaust (6) which may, if required, connect to a filter located in a fluidizing vessel (7). A mechanical size reduction device (8) may be used with a grading device (18) inserted ahead of the size reduction device. The grading device may consist of a mill or a rotating hammer mill installed inside or outside of the fluidized bed reactor, counteracting any enlargement of the grain size, and simultaneously producing new granulation nuclei and heat transfer surfaces (9).

BRIEF DESCRIPTION OF THE DRAWING

The drawing shows an embodiment of the invention.

Referring further to the drawing, the process of this invention generally proceeds as follows: dried residues, having a certain particle size distribution and being largely free of the desired product, are introduced into the reactor as a fluidizing layer (2). At elevated temperatures, the completely heated or partially molten distillation residue is fed through distillaton residue feed line (10), combined with the atomizing gas, inert under the reaction conditions, which is fed via atomizing gas feed line (11), and sprayed into the fluidizing layer through a product input jet (4). During this process, the individual particles of the fluidizing medium are surrounded by a thin layer of the distillation residue from which the desired product is very quickly distilled. The energy required for evaporating the desired product is either partially or completely supplied by the fluidizing gas which is introduced via fluidizing gas feed line (12) and the fluidizing gas entry tray (3). The mixture of vapors, desired products, and fluidizing gas is removed via offgas exhaust line 6 to a filter in a fluidizing vessel (7) where the dust is removed. Subsequently, the desired product is liquidified in condenser (13) and separated from the fluidizing gas. Via exhaust line (14), a blower (19), and a heat exchanger (21), the fluidizing gas is recycled to the fluidizing gas feed line (12). A gas excess in the fluidizing gas circulation, resulting from the addition of atomizing gas, can, if so required, be discharged by excess gas line (20). The excess amount of gas may be avoided by means of separating part of the recycling fluidizing gas, compressing this gas by means of a compresser (22), heating it by means of a heat exchanger (23) and using it as a recycle atomizing gas via atomizing gas feed line (11). The desired product is transported to a storage vessel via desired product discharge line (15). The dry residue, free of desired product, is continuously discharged from the fluidized bed by means of a screw conveyor via discharge (5), is generally combined with the product of the grading device (18) and combined with the dust from filter (7) via discharge line (16) and is removed (17).

The following are the required reaction conditions:

As already indicated, the fluidizing medium, which primarily consists of residue free of the desired material, must have certain particle sizes. Particle sizes of 0.5 micron to 5000 microns, preferably of 100 microns to 2000 microns, have proven to work particularly well and are therefore preferably used. If the particle sizes are too small, the fluidized material is discharged pneumatically. If particles are too large, they settle on the fluidizing gas entry tray and plug it. The particle size may be controlled by the abrasion in the fluidized bed or by mechanical size reduction devices in or outside of the fluidized bed. Abrasion is a function of the fluidization number, that is the velocity W in the empty and unobstructed space relative to the fluidization velocity WL and the height of the fluidized bed. The abrasion rate increases with rising fluidization number and bed type.

The distillation residue is heated and is sprayed into the fluidized bed at temperatures of 50° C. to 300° C., preferably of 100° C. to 230° C. via an introduction device such as jets, preferably one or more one- or two-substance jets. The jets may be arranged in such a manner that they spray from the top, from the side, from the bottom, or directly into the fluidized bed. For reasons of construction and process engineering, the arrangement from the side has proven to be advantageous. With the arrangement of this drawing, the jets must be installed above the gas entrance tray in such a manner that the atomized distillation residue does not hit the tray and that a plugging of the tray is avoided. The free rate of the nozzle with distillation residue is a function of the size of the fluidized bed and is approximately 1 kilogram per hour to 500 kilograms per hour, preferably 50 kilograms per hour to 500 kilograms per hour, per square meter of gas entry tray. Under the described reaction conditions, inert gasses may be used as atomizing gas. Preferably used is nitrogen in quantities of 0.1 kilogram to 5 kilograms, preferably of 0.5 kilogram to 1.5 kilograms, per kilogram of distillation residue with the pressure of the atomizing gas being 1.5 bars to 10 bars, preferably 2 bars to 4 bars.

Gases suitable for atomizing may also be used as fluidized gas. Preferably used is nitrogen which is preheated to a temperature of 100° C. to 350° C., preferably to 150° C. to 280° C., and is introduced via the fluidizing gas entry tray. Under normal conditions, the free stream velocity for the fluidizing gas (20° C. and 760 millimeters Hg) is 0.1 meter per second to 2 meters per second, preferably 0.2 meter per second to 0.8 meter per second. The free stream velocities under operating conditions can be calculated from these data. In addition to this, the void fractions $\epsilon_L$ at the fluidizing point can be calculated from the free stream velocity of the fluidizing gas and the particle diameter of the fluidizing layer. The void fractions show values of 0.4 to 0.75, preferably 0.5 to 0.7.

The desired product is separated in the fluidized layer essentially under atmospheric pressure and at temperatures from 140° C. to 280° C., preferably from 160° C. to 250° C. The required energy is preferably introduced via the fluidizing gas and is transferred to the fluidizing medium. Under certain circumstances, however, it may be appropriate to install heating surfaces such as heating panels or pipe bundles into the fluidizing layer.

The residence time in the fluidizing layer of the residue, which is essentially free of the desired product, is approximately 0.1 hour to 10 hours, preferably 0.1 hour to 3 hours. After being discharged, the residue has a residual content of desired product of 0.1 weight percent to 2.0 weight percent, preferably of 0.3 weight percent to 1 weight percent.

The residue is discharged from the fluidizing layer via a discharge. An essential factor is that the no longer whirling residue particles do not agglomerate at the fluidizing gas entry tray ports, thereby stopping the fluidizing process, but that care is taken that the settled residue particles are transported to the discharge and are prevented from returning by tilting the fluidizing gas entry trays towards the discharge, by installing corresponding fixtures or by using gas entry ports with fluidizing gas jets directed toward the discharge. The residue may be discharged, for instance, by a bottom drain or discharge shaft with the amount discharged being controlled, for instance, by a cover, a gate, a bucket wheel conveyor, or preferably screw conveyors.

The discharged residue is combined with the residue from the dust removal filters and is, for instance, burned.

As already described, the dust is removed from the exhausted mixture of vaporous desired product or desired product mixture and fluidizing gas which has a desired product content of 0.001 kilogram to 1 kilogram, preferably of 0.1 kilogram to 1 kilogram of desired product per kilogram of fluidizing gas and is subsequently cooled to temperatures of 25° C. to 160° C. in a condenser. Hereupon, the desired product or the desired product mixture liquifies, separates from the fluidizing gas, and is subsequently transported into a storage vessel.

Via exhaust line (14), a blower (19), and a heater (21) the fluidizing gas is recycled to feed line (12). A gas excess in the fluidizing gas circulation, resulting from the addition of atomizing gas, can, if so required, be discharged by line (20). The excess amount of gas may be avoided by means of separating part of the recycling fluidizing gas, compressing this gas by means of a compressor (22), heating it by means of a heat exchanger (23) and using it as a recycle atomizing gas via atomizing gas feed line (11).

The following examples are intended to explain the invention without restricting its coverage.

EXAMPLES

Into a cylindrical fluidized bed reactor having a diameter of 6 centimeters and a height of 30 centimeters, heated electrically from the outside, equipped with a fritt as gas entry tray, a two-component nozzle installed on the side 5 centimeters above the gas entry tray, and a screw conveyor as discharge are introduced 80 grams of dry residue having an average grain diameter of 0.2 millimeter to 1 millimeter. The nitrogen fluidizing gas, which is heated in a heat exchanger, is introduced via the gas entry tray and the distillation residue having an average desired product content of 50 weight percent to 75 weight percent is introduced via the two-component input jet in the form of a melt using nitrogen as atomizing gas.

The gas is removed from the mixture of vaporous desired product and the nitrogen using a wire cloth filter and the mixture is cooled in a condenser and is separated.

For the following experiment, two different distillation residues were used. For the one test, a distillation residue (I) was used which came from a phosgenation of toluene diamine to toluene diisocyanate using monochlorobenzene as solvent and which contained 68.5 weight percent of toluene diisocyanate (TDI) as the desired substance to be reclaimed. For the Examples on reclaiming a solvent boiling at temperatures higher than toluene diisocyanate a distillation residue (II) was selected which was obtained from a phosgenation of toluene diamine to toluene diisocyanate with diethylisophthalate as solvent and contained 57.0 weight percent of diethylisophthalate (DEIP) as substance to be reclaimed.

The following table contains a listing of the test conditions, additional characteristic data, and test results for the 7 tests which were conducted as examples. Test data which were the same for all 7 examples and which are already listed in the above instructions are not shown in the Table.

TABLE

Test Data for Examples 1 to 7

| | Units | Examples | | | | | | |
|---|---|---|---|---|---|---|---|---|
| | | 1 | 2 | 3 | 4 | 5 | 6 | 7 |
| Fluidizing Medium | | | | | | | | |
| Temperature | °C. | 240 | 170 | 150 | 250 | 250 | 270 | 280 |
| Distillation Residue | Type | I | I | I | I | II | II | II |
| Amount fed via line (10) | kg/h | 0.535 | 0.247 | 0.263 | 1.324 | 0.438 | 0.827 | 1.269 |
| Temperature | °C. | 190 | 150 | 150 | 200 | 220 | 220 | 220 |
| Atomizing Gas | | | | | | | | |
| Amount fed via line (11) | kg/h | 0.50 | 0.27 | 0.16 | 0.73 | 0.42 | 0.38 | 1.0 |
| Temperature | °C. | 190 | 150 | 150 | 200 | 220 | 220 | 220 |
| Supply Pressure | bar | 3 | 2 | 1.5 | 5.5 | 2.5 | 2.5 | 9 |
| Fluidizing Gas | | | | | | | | |
| Amount fed via line (12) | kg/h | 1.0 | 1.0 | 1.3 | 2.0 | 1.0 | 1.5 | 12.5 |
| Temperature | °C. | 260 | 185 | 165 | 280 | 270 | 295 | 290 |
| Fluidizing gas velocity calculated for normal conditions | m/sec | 0.12 | 0.12 | 0.16 | 0.24 | 0.12 | 0.18 | 1.5 |
| Fluidizing Properties | | | | | | | | |
| Void Fraction $\epsilon_L$ at the fluidizing point | | 0.6 | 0.7 | 0.75 | 0.55 | 0.6 | 0.5 | 0.45 |
| Average residence time | min | 27 | 66 | 55 | 12 | 27 | 12 | 9 |

TABLE-continued

Test Data for Examples 1 to 7

| | Units | 1 | 2 | 3 | 4 | 5 | 6 | 7 |
|---|---|---|---|---|---|---|---|---|
| of the residue in the fluidizing bed | | | | | | | | |
| Discharged Product | Type | TDI | TDI | TDI | TDI | DEIP | DEIP | DEIP |
| Product content of the gas mixture removed via line (6) | % by weight | 19.5 | 11.7 | 11.0 | 24.9 | 14.9 | 20.0 | 5.1 |
| Condenser temperature (13) | °C. | 80 | 80 | 70 | 80 | 90 | 90 | 90 |
| Condensate transported via line (15) | kg/h | 0.348 | 0.159 | 0.170 | 0.868 | 0.239 | 0.448 | 0.664 |
| Reclaiming yield | % | 95.0 | 94.0 | 94.3 | 95.7 | 95.9 | 95.1 | 91.8 |
| Residue Discharge | | | | | | | | |
| Amount of residue removed via line (17) | kg/h | 0.177 | 0.073 | 0.087 | 0.413 | 0.181 | 0.402 | 0.551 |
| Residual desired product content | % by weight | 0.7 | 1.6 | 1.8 | 0.5 | 0.85 | 1.2 | 0.3 |
| Range of ring sizes | diameter in mm | 0.1–1.2 | 0.1–3.0 | 0.1–3.5 | 0.05–1.1 | 0.1–1.3 | 0.05–1.2 | 0.05–1.1 |

Averaging the tests with respect to the desired product showed a high reclaiming yield between approximately 92 and 96 percent. Only small quantities of the desired product were discharged with the dry residue. The resultant desired product losses were 0.2 percent (Example 4) to 0.9 percent (Example 3) with respect to the toluene diisocyanate, and 0.2 percent (Example 7) to 1.0 percent (Example 6) concerning the diethylisophthalate. The greatest part of the yield difference to 100 percent is recycled with the residual content in the offgas (14) following the condenser (13). By recycling the fluidizing and atomizing gas, the reclaiming yield can thus be increased further.

The embodiments of the invention in which an exclusive property or privilege is claimed as defined as follows:

1. A process for the separation of toluene diisocyanates and/or higher boiling solvents from distillation residues obtained during the reaction of toluene diamine with phosgene in the presence of solvents and subsequent distillation of the reaction solution comprising treating the distillation residues in a fluidized bed at temperatures of 140° C. to 280° C.

2. The process of claim 1 wherein void fractions $\epsilon_L$ of 0.4 to 0.75 are employed.

3. The process of claim 1 wherein solid material, of an average particle size of 0.5 micron to 5000 microns is initially placed into a fluidized bed vessel.

4. The process of claim 1 wherein feeding the fluidizing gas is done at an initial flow velocity of 0.1 meter per second to 2 meters per second at 20° C. and 760 mmHg.

5. The process of claim 1 comprising recycling nitrogen as the fluidizing gas.

6. The process of claim 1 comprising injecting the distillation residue by a two-product jet into the fluidized bed and injecting an atomized gas into the fluidized bed with a supply pressure of 1.5 bars to 10 bars.

7. The process of claim 1 comprising preheating fluidizing gas for energy to evaporate the desired product or products in the fluidized bed.

8. The process of claim 1 comprising introducing energy for evaporating the desired product or product mixture in the fluidized bed via the wall of the fluidized bed vessel and/or through heat exchange surfaces installed in the fluidized bed.

9. A process for the separation of toluene diisocyanates and/or higher boiling solvents from distillation residues obtained during the reaction of toluene diamine with phosgene in the presence of solvents and subsequent distillation of the reaction solution comprising establishing a fluidizing bed by placing an initial material of an average particle size of 0.5 micron to 5000 microns into a fluidized bed reactor; feeding a fluidizing gas to establish a specified void fraction of 0.4 to 0.75, at a velocity of 0.1 meter per second to 2 meters per second at normal conditions of 20° C. and 760 mmHg and which said fluidizing gas is recycling nitrogen; injecting the distillation residue containing a desired product by a two-product jet into the fluidized bed and injecting the atomizing gas into the fluidized bed with a supply pressure of 1.5 bars to 10 bars.

* * * * *